United States Patent [19]

Takahashi et al.

[11] Patent Number: 4,716,235

[45] Date of Patent: Dec. 29, 1987

[54] PROCESS FOR PREPARING N-[1(S)-ETHOXYCARBONYL-3-PHENYL-PROPYL]-L-ALANYL-L-PROLINE

[75] Inventors: Satomi Takahashi, Kobe; Kenji Inoue; Yoshifumi Yanagida, both of Takasago; Takehisa Ohashi, Kobe; Kiyoshi Watanabe, Akashi, all of Japan

[73] Assignee: Kanegafuchi Kagaku Kogyo Kabushiki Kaisha, Osaka, Japan

[21] Appl. No.: 900,051

[22] Filed: Aug. 25, 1986

[30] Foreign Application Priority Data

Aug. 27, 1985 [JP] Japan ................. 60-188243

[51] Int. Cl.$^4$ ............................................ C07D 207/09
[52] U.S. Cl. ................................................... 548/533
[58] Field of Search ............................ 548/533, 227

[56] References Cited

U.S. PATENT DOCUMENTS

| | | | |
|---|---|---|---|
| 2,406,186 | 8/1946 | Baldwin et al. | 548/227 X |
| 2,657,972 | 11/1953 | Woodward | 548/227 X |
| 3,196,169 | 7/1965 | Alburn et al. | 548/227 X |
| 4,267,344 | 5/1981 | Halstrom et al. | 548/227 |
| 4,496,542 | 1/1985 | Skiles et al. | 514/2 |

OTHER PUBLICATIONS

Wyvratt, et al.; J. Org. Chem.; 49; (1984); pp. 2816–2819.

Kaltenbronn, et al.; Organic Preparations & Procedures Intl., 15 (1982); pp. 35–40.

Katritzky, et al.; "Comprehensive Heterocyclic Chemistry"; vol. 6; Part 4B (1948); pp. 214–215; Pergamon Press–Oxford, N.Y.

*Primary Examiner*—Joseph Paul Brust
*Attorney, Agent, or Firm*—Armstrong, Nikaido, Marmelstein & Kubovcik

[57] ABSTRACT

A process for preparing N-[1(S)-ethoxycarbonyl-3-phenylpropyl]-L-alanyl-L-proline, which comprises reacting N-carboxyanhydride of N-[1(S)-ethoxycarbonyl-3-phenylpropyl]-L-alanine with L-proline in the presence of a base. According to the process, enalapril can be prepared economically, easily and effectively.

6 Claims, No Drawings

PROCESS FOR PREPARING N-[1(S)-ETHOXYCARBONYL-3-PHENYL-PROPYL]-L-ALANYL-L-PROLINE

BACKGROUND OF THE INVENTION

The present invention relates to a process for preparing N-[1(S)-ethoxycarbonyl-3-phenylpropyl]-L-alanyl-L-proline (hereinafter referred to as "enalapril") having the formula (I):

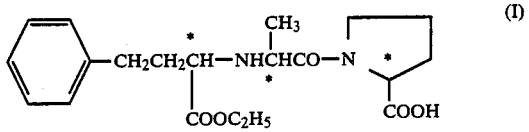

wherein an asterisk represents (S)-configuration with respect to the asymmetric carbon atom, which is a main component of N-[1(S)-ethoxy-carbonyl-3-phenyl-propyl]-L-aranyl-L-proline maleate (USAN: Enalapril Maleate) which is expected to be used as an antihypertensive agent due to an excellent Angiotensin Converting Enzyme (ACE) inhibitory activity.

As a method for preparing the enalapril, there has already been known a method by a reductive amination reaction, in which a Schiff's base (IV) obtained by condensing L-alanyl-L-proline (III) with ethyl α-oxo-γ-phenylbutyrate (II) is reduced with hydrogen gas in the presence of catalyst such as palladium/carbon or sodium cyanoborohydride ($NaBH_3CN$) [Japanese Unexamined Patent Publication No. 81845/1980 and J. Org. Chem. 49 (15), 2816 (1984)].

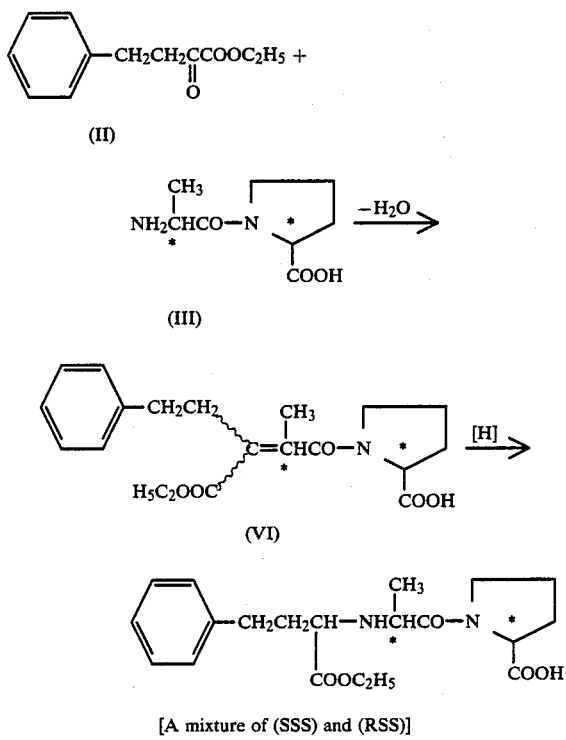

[A mixture of (SSS) and (RSS)]

ACE inhibitory activity of the enalapril is closely related to a configuration at an asymmetric carbon atom. For the desired activity, it is necessary that the enalapril is an optically active compound with (S)-configuration with respect to all the three asymmetric carbon atoms, i.e. (SSS)-configuration. According to the above method for synthesizing the enalapril by the reductive amination reaction, however, a mixture of (SSS)-configuration and (RSS)-configuration is prepared since both (S)-configuration and (R)-configuration of N-[1-ethoxycarbonyl-3-phenylpropyl]-L-alanyl-L-proline are produced with respect to the asymmetric carbon atom in the phenylbutyric acid part of the compound produced by the reduction of the Schiff's base having the formula (VI). For this reason, various studies have been made in order to advantageously obtain the enalapril with the desired (SSS)-configuration. When the catalytic reduction is carried out with a catalyst of palladium/carbon, well utilizing the steric structure of the L-alanyl-L-proline portion, the asymmetric induction occurs to some extent. However, a ratio of (SSS)-configuration/(RSS)-configuration is still 62/38 and thus a complicated optical resolution procedure is required in order to obtain the desired compound with (SSS)-configuration, and moreover, a yield of the desired compound with (SSS)-configuration is quite low, i.e. less than 50% due to the production of a large amount of the compound with (RSS)-configuration, although each reaction proceeds in high efficiency. Therefore, starting materials which are expensive and prepared by many steps, ethyl α-oxo-γ-phenylbutyrate (II) and L-alanyl-L-proline (III), may be wasted by this method. Also, in the reductive amination reaction, when the reaction to form the Schiff's base and the reduction of the Schiff's base are carried out separately, even (SRS)-configuration and (RRS)-configuration derived from racemization of the alanine portion are also inadvantageously by-produced in addition to (SSS)-configuration and (RSS)-configuration, since the Schiff's base prepared in the reaction substantially has a tendency to cause racemization. In order to avoid racemization of the Schiff's base, it has been attempted to prepare the Schiff's base in situ in the reduction system. However, ethyl α-oxo-γ-phenylbutyrate (II), which is easily reduced by nature, is not only used for producing the Schiff's base but also reduced to form a by-product such as ethyl α-hydroxy-γ-phenylbutyrate, which results in a competitive wasteful consumption of the compound (II), and thus 2 to 3 times molar amount of ethyl α-oxo-γ-phenylbutyrate must be used, which leads to a disadvantage in an operation such that the complicated extraction procedure is required for isolating the desired compound from the reaction mixture including a large amount of ethyl α-hydroxy-γ-phenylbutyrate by-produced.

As aforementioned, the method by the reductive amination reaction cannot be advantageous for the industrial production of the enalapril in viewpoint of economy and operability.

As the result of the present inventors' continuous study to establish an economical, simple and efficient process of the industrial production of the enalapril, it was found that N-carboxyanhydride of N-[1(S)-ethoxycarbonyl-3-phenylpropyl]-L-alanine can be reacted with L-proline quite easily in the presence of a base to produce the enalapril with almost quantitative yield.

SUMMARY OF THE INVENTION

According to the present invention, there is provided a process for preparing N-[1(S)-ethoxycarbonyl-3-phenylpropyl]-L-alanyl-L-proline, which comprises reacting N-carboxyanhydride of N-[1(S)-ethoxycarbonyl-3-phenylpropyl]-L-alanine with L-proline in the presence of a base.

DETAILED DESCRIPTION

The process of the present invention is shown by the following reaction scheme.

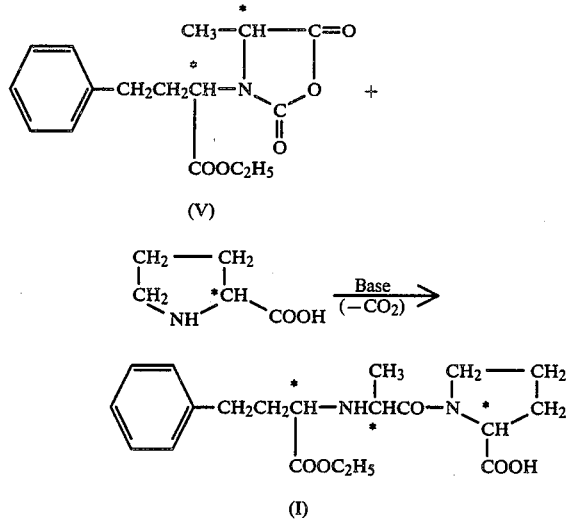

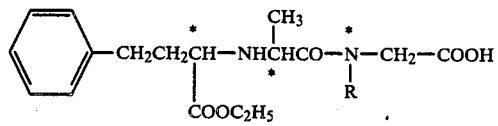

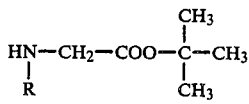

As shown by the above reaction scheme, the process of the present invention is characterized by the fact that N-carboxyanhydride of N-[1(S)-ethoxycarbonyl-3-phenylpropyl]-L-alanine is reacted with L-proline in the presence of a base to effectively produce the enalpril.

Various compounds with the ACE inhibitory activity having the general formula:

wherein R is phenylethylene group, 3-pyridylmethyl group or an alkoxy group such as benzyloxy group, has already been synthesized by reacting N-carboxyanhydride of N-[1(S)-ethoxycarbonyl-3-phenylpropyl]-L-alanine (V) with a tert-butylester of N-substituted glycine having the general formula:

$$HN-CH_2-COO-C(CH_3)_3$$
 $$|$$
 $$R$$

wherein R is as defined above, yield in this step being from 50 to 70%, and then carrying out a deesterification reaction with an acid (Japanese Unexamined Patent Publication Nos. 175152/1982, 176941/1982 and 130844/1984). The above method, however, does not suggest the process of the present invention since amine component is limited to only tert-butylesters of N-substituted glycine.

The present invention was completed from the finding that N-carboxyanhydride of N-[1(S)-ethoxycarbonyl-3-phenylpropyl]-L-alanine (V) is quite efficiently reacted with L-proline in the presence of a base to give the desired enalapril in a quantitative yield with substantially no side reaction. According to the process of the present invention, it is not required to protect carboxyl group of the amine component (L-proline) by esterification and thus deesterification is not also required after the reaction with N-carboxyanhydride (V). The process of the present invention can produce the desired enalapril directly in a high yield by a simple procedure of only neutralization of acid and base.

Various processes for preparing N-[1(S)-ethoxycarbonyl-3-phenylpropyl]-L-alanine, which is a starting material for preparing N-carboxyanhydride (V), have already been reported [Organic Preparations and Procedures INT, 15, 35 to 40 (1983), Tetrahedron Letters 25, 1143 to 1146 (1984) and Japanese Unexamined Patent Publication Nos. 112359/1982, 116046/1982 and 65057/1984]. For example, it can also be prepared easily by catalytically reducing N-[1(S)-ethoxycarbonyl-3-phenylpropyl]-L-alanine which is prepared by the asymmetric addition reaction between ethyl β-benzoyl acrylate and an alkali metal salt of L-alanine (Japanese Unexamined Patent Publication No. 19483/1985).

N-carboxyanhydride (V) can be easily prepared, as in the same manner as a usual process for preparing N-carboxyanhydride of α-amino acid, by heating under reflux N-[1(S)-ethoxycarbonyl-3-phenylpropyl]-L-alanine in methylene chloride containing phosgene, as described in Japanese Unexamined Patent Publication No. 175152/1982, or by heating trichloromethylchloroformate and N-[1(S)-ethoxycarbonyl -3-phenylpropyl]-L-alanine in the presence of a small amount of active carbon in an inactive solvent, as will be shown in Reference Examples.

In the peptide bond forming reaction between N-carboxyanhydride (V) and L-proline, it is assumed that L-proline participates in the reaction by forming a salt with the base. That is, the reactant as proline component varies with the employed base; when a hydroxide or carbonate of alkali metal or alkaline earth metal is used as the base, it is assumed that an alkali metal salt or an alkaline earth metal salt of L-proline participates in the reaction, and when a secondary amine, a tertiary amine or a quarternary ammonium hydroxide is used as the base, it is assumed that an ammonium salt of L-proline participates in the reaction. Accordingly, it is possible to use such a salt of L-proline previously prepared and separated.

Examples of the base are, for instance, inorganic bases such as hydroxide of lithium, sodium, potassium, calcium or magnesium, carbonate of lithium, sodium or potassium, hydrogencarbonate of lithium, sodium or potassium; and amine other than a primary amine, i.e., a secondary amine such as dimethylamine, diethylamine, diethanolamine or dicyclohexylamine, a tertiary amine such as trimethylamine, triethylamine, tripropylamine, tributylamine, triamylamine, triethanolamine, pyridine or an N-alkylmorpholine; a quarternary ammonium hydroxide such as tetramethyl, tetraethyl, tetrapropyl, tetrabutyl, tetraamyl, tetrahexyl, benzyltrimethyl or benzyltriethyl ammonium hydroxide.

The peptide bond forming reaction of the present invention can be carried out in an aqueous medium, preferably in a mixture of water and organic solvent. A mixture of water and a solvent having a high compatibility with water such as acetone, dioxane, tetrahydrofuran, acetonitrile or lower alcohols is preferably used. Although a yield is generally poor when a solvent having a low compatibility with water such as ethyl acetate, methylene chloride, or hexane is used, it is also possible to increase the yield by vigorously stirring the reaction mixture.

The reaction of the present invention can be carried out by adding N-carboxyanhydride (V) dissolved in the organic solvent to a solution of the salt of L-proline previously prepared from L-proline and the base in equimolar or a little excess amount of L-proline, with stirring under cooling. However, the present invention is not limited to such procedure and another various procedures can also be applied.

It is preferable that the amount of L-proline is not less than an equimolar amount of N-carboxyanhydride (V), usually from 1 to 1.5 times molar amount, in viewpoint of a good yield and simple procedure of isolating the desired compound.

Since the pH of the reaction system generally becomes lowered as the reaction proceeds, the pH is maintained within the alkaline range, preferably from about pH 9 to 10 in order to avoid the production of the by-product. Although the reaction temperature is not particularly limited and the reaction well proceeds within the range of from $-20°$ C. to room temperature, it is preferable that the reaction is carried out at relatively low temperature. The reaction rate is low at a low temperature and high at a high temperature as in the case of the usual reaction. It is enough that the reaction is carried out for 10 to 20 minutes at about $0°$ C. In order to stop the reaction, the reaction mixture is acidified by adding a mineral acid to the reaction system to decompose (decarboxylation) a carbamic acid produced in the reaction.

The isolation of the obtained enalapril (I) can be carried out by the usual separation procedure by extraction; after the reaction mixture is concentrated under reduced pressure to distill away the organic solvent and the pH of the concentrate is adjusted to the isoelectric point of the enalapril (pI 4.2), extraction with ethyl acetate is carried out and the extract is concentrated under reduced pressure.

By controling the above reaction condition, the enalapril can be prepared in a substantially quantitative yield of about 95% based on the used N-carboxyanhydride (V). Also, as the occasion demands, the desired compound can be isolated as the enalapril maleate of white crystal by adding an equimolar amount of maleic acid based on the enalapril.

The present invention is more particularly described and explained by the following Reference Examples and Examples. It is to be understood, however, that the present invention is not limited to these Examples and various changes and modifications may be made without departing from the scope of the present invention.

REFERENCE EXAMPLE 1

Synthesis of N-[1(S)-ethoxycarbonyl-3-phenylpropyl]-L-alanine. N-carboxyanhydride]

A 2 l four neck round bottom flask equipped with a reflux condenser was charged with 25 g (89.6 mmol) of N-[1(S)-ethoxycarbonyl-3-phenylpropyl]-L-alanine and 500 ml of dry dichloromethane, into which 32 g of phosgene was introduced at room temperature with stirring, and then the mixture was heated under reflux on an oil bath at $50°$ C. for 8 hours. Then, after distilling away most of dichloromethane including phosgene from the reaction mixture, the residue was transferred into a 200 ml recovery flask, and further dichloromethane was completely removed under reduced pressure, which results in a white solid from the oily residue, to give 27.5 g of crystalline N-[1(S)-ethoxycarbonyl-3-phenylpropyl]-L-alanine.N-carboxyanhydride in a quantitative yield (purity: 99%).

Melting point: $67°$ to $68°$ C. (measured in a sealed capillary vessel after substituting with nitrogen gas).

$[\alpha]_D^{25} = +11.8$ (c=1, acetonitrile).

Infrared absorption spectrum (cm$^{-1}$): 2980, 2930, 1845, 1770, 1725, 1495, 1450, 1420, 1380, 1290 and 1240

$^1$H nuclear magnetic resonance spectrum (CDCl$_3$, $\delta$): 7.25 (m, 5H, ArH$_{2-6}$), 4.4 to 4.0 (m, 4H, PhCH$_2$CH$_2$CH, Ala a-H, OCH$_2$CH$_3$), 2.8 (m, 2H, PhCH$_2$), 2.3 (m, 2H, PHCH$_2$CH$_2$), 1.5 (d, 3H, Ala-CH$_3$) and 1.25 (t, 3H, OCH$_2$CH$_3$).

REFERENCE EXAMPLE 2

[Synthesis of N-[1(S)-ethoxycarbonyl-3-phenylpropyl]-L-alanine.N-carboxyanhydride]

A 2 l four neck round bottom flask equipped with a reflux condenser was charged with 25 g (89.6 mmol) of N-[1(S)-ethoxycarbonyl-3-phenylpropyl]-L-alanine, 500 mg of active carbon and 500 ml of dry dichloromethane, to which 16 g of trichloromethylchloroformate was added through a dropping funnel at room temperature for about 20 minutes with stirring, and the mixture was heated under reflux on the oil bath for 5 hours. After further adding 16 g of trichloromethyl formate dropwise, the mixture was heated under reflux for 5 hours. Then, after distilling away most of dichloromethane including phosgene from the reaction mixture, the residue was cooled to room temperature and filtered off to remove the active carbone. The obtained filtrate was transferred into a 200 ml recovery flask, and dichloromethane was completely removed under reduced pressure, which resulted in a white solid from the oily residue, to give 28.0 g of crystalline N-[1(S)-ethoxy-carbonyl-3-phenylpropyl]-L-alanine.N-carboxyanhydride in a quantitative yield (purity: 98%).

The obtained product had the same physical properties as those in Reference Example 1.

REFERENCE EXAMPLE 3

[Measurement of the purity of N-[1(S)-ethoxycarbonyl-3-phenylpropyl]-L-alanine.N-carboxyanhydride]

The purity of the obtained products were measured by reacting the obtained N-carboxyanhydride with ethanol in the presence of a base to prepare N-[1(S)-ethoxycarbonyl-3-phenylpropyl]-L-alanine ethyl ester, which was then subjected to a high performance liquid chromatography (hereinafter referred to as "HPLC"). More particularly, about 100 mg of the sample of the N-carboxyanhydride was put in a 10 ml messflask, to which absolute ethanol containing 0.3% (wv) of triethylamine was added to give 10 ml of the solution and the esterification was carried out by stirring the solution with magnetic stirrer at room temperature for 10 minutes. To 1.0 ml of the thus obtained solution sulfuric acid was added to adjust the pH of the solution to 2 to 3, which was stirred at room temperature for about 10 minutes. Then 4 ml of ethanol solution containing 10 mg of n-propylbenzoic acid (internal standard agent) was added to the sample, the mixture was subjected to the analysis by the column chromatography under the following conditions.

Column: Finepack SIL $C_{18}$ (made by Japan Spectroscopic Co., Ltd.) 4.6 mm ID×250 mm.

Mobile phase: 100 mM phosphate buffer (pH 7.0)methanol =40/60 (vv).

Flow rate: 1.0 ml min.

Detection: 210 nm.

EXAMPLE 1

A solution of a sodium salt of proline was prepared by adding water to a mixture of 2.30 g of L-proline, 20 ml of 1N sodium hydroxide and 2.12 g of sodium carbonate so as to make a total amount of 100 ml. A 50 ml recovery flask was charged with 5 ml of the thus obtained solution and each 5 m; of various solvents shown in Table 1, to which 254 mg of N-[1(S)-ethoxycarbonyl-3-phenylpropyl]-L-alanine.N-carboxyanhydride dissolved in 5 ml of the solvent at 0° C. was rapidly added while cooling with ice at 0° C., and the mixture was stirred at 0° C. for 1 hour. After adjusting the pH of the reaction mixture to about 1 with 6N HCl, water was added so as to make a total amount of 100 ml. The produced enalapril (hereinafter referred to as "EPL") was measured by HPLC in the following conditions to give the results as shown in Table 1.

Colomn: Finepack SIL $C_{18}$ (made by Japan Spectroscopic Co., Ltd.) (4.6 mm ID×250 mm).

Mobile phase: 60 mM phosphate buffer (pH 2.5)methanol=63/37 (vv).

Flow rate: 1.5 ml/min.

Detection: 210 nm.

Internal standard: L-5-benzyl hydantoin.

TABLE 1

| Solvent | Amount of the produced EPL (mg) |
|---|---|
| Acetone | 280.3 |
| Acetonitrile | 262.3 |
| THF | 271.8 |
| Dioxane | 286.7 |
| Ether | 228.1 |
| DMF | 206.3 |
| Ethanol | 236.7 |
| Methanol | 123.2 |
| Chloroform | 22.8 |
| Dichloroform | 1.8 |
| Ethyl acetate | 68.1 |
| Methyl ethyl ketone | 81.3 |
| Water | 184.6 |

EXAMPLE 2

A 50 ml recovery flask was charged with a solution of 115.1 mg of L-proline and each 1 mmole of various bases shown in Table 2 dissolved in 5 ml of water and 5 ml of acetone, to which a solution of 254 mg of N-[1(S)-ethoxycarbonyl-3-phenylpropyl]-L-alanine.N-carboxyanhydride dissolved in 5 ml of acetone at 0° C. was rapidly added while cooling with ice at 0° C., and the mixture was stirred at 0° C. for 1 hour. After adjusting the pH of the reaction mixture to about 1 with 6 N HCl, water was added so as to make a total amount of 100 ml. The produced EPL was measured by HPLC in the same manner as in Example 1.

The results are shown in Table 2.

TABLE 2

| Base | Amount of the produced EPL (mg) |
|---|---|
| NaOH (1 mmol) + $Na_2CO_3$ (1 mmol) | 280.3 |
| LiOH (1 mmol) + $Na_2CO_3$ (1 mmol) | 292.7 |
| KOH (1 mmol) + $Na_2CO_3$ (1 mmol) | 260.9 |
| NaOH | 271.8 |
| $Mg(OH)_2$ | 91.4 |
| $Na_2CO_3$ | 284.1 |
| $NaHCO_3$ | 266.5 |
| $NEt_4OH$*1 | 284.2 |
| $NEt_3$*2 | 280.0 |
| $HNEt_2$*3 | 287.3 |
| DCHA*4 | 268.8 |
| None (control) | 0 |

Note
*1 Tetraethylammoniumhydroxide
*2 Triethylamine
*3 Diethylamine
*4 Dicyclohexylamine

EXAMPLE 3

A 20 ml recovery flask was charged with 6 ml of the solution of sodium salt of proline prepared in Example 1 and 6 ml of acetone. To the mixture a solution of 304.9 mg of N -[1(S)-ethoxycarbonyl-3-phenlpropyl]-L-alanine.N-carbonxyanhydride dissolved in 7 m? of ace was rapidly added at each temperature shown in Table 3, to which acetone was added so as to make a total amount of 20 ml and the mixture was stirred at the same temperature for the time shown in Table 3. Then, a 10 ml messflask was charged with 2 ml of the reaction mixture and the pH of the reaction mixture was adjusted to about 1 with 6N HCl. After water was added so as to make a total amount of 10 ml, the produced EPL was measured by HPLC in the same manner as in Example 1.

The results are shown in Table 3.

TABLE 3

| Reaction temperature (°C.) | Reaction time (°C.) | Amount of the produced EPL (mg) |
|---|---|---|
| −10 | 20 | 278.9 |
| −10 | 40 | 345.6 |
| −10 | 60 | 363.7 |
| 0 | 20 | 343.9 |
| 0 | 40 | 357.7 |
| 0 | 60 | 336.1 |
| 10 | 20 | 338.2 |
| 10 | 40 | 344.6 |
| 10 | 60 | 341.0 |

EXAMPLE 4 A 100 ml recovery flask was charged with 15 ml of the solution of sodium salt of proline prepared in Example 1 and 15 ml of acetone. To the mixture a solution of 762 mg of N-[1(S)-ethoxycarbonyl-3-phenylpropyl]-L-alanine.N-carboxyanhydride dissolved in 15 ml of acetone at 0° C. was rapidly added, and the mixture was stirred at 0° C. for 30 minutes. After adjusting the pH of the reaction mixture to about 2 with 6 N HCl, acetone was added so as to make a total amount of 200 ml. One ml of the obtained acetone solution was analyzed by HPLC in the same manner as in Example 1, which showed the production of 1.021 g of EPL.

After adjusting the pH of the acetone solution to 4.2 with 1N NaOH, acetone was distilled away from the solution under reduced pressure. The obtained aqueous layer was saturated with a salt, and the obtained saturated salt solution was extracted with 100 ml of ethyl acetate three times. The extracted ethyl acetate layer was dried over anhydrous sodium sulfate and the solvent was distilled away under reduced pressure to give 1.115 g of oily EPL (purity: 87 %).

REFERENCE EXAMPLE 4

[Preparation of enalapril maleate]

To the oily EPL obtained in Example 4, 3.4 ml of acetonitrile was added and the mixture was heated to 70° C., to which a solution of 334 mg of maleic acid dissolved in 5 ml of acetonitrile at 70° C. was added. The reaction mixture was gradually cooled to room temperature and was allowed to stand at 5° C. for one night to deposit crystal. The obtained crystal was filtered off, washed with ether, and dried to give 1.022 g of crude crystal. The obtained crystal and 476 mg of white solid obtained from the filtrate by distilling away the solvent under reduced pressure were recrystallized from acetonitrile to give 1.106 g of EPL as white crystal.

Melting point: 145° to 146.5° C. (the value described in the literature: 143° to 144.5° C.). $^1$H nuclear magnetic resonance spectrum (D$_2$O): δ1.30 (t, 3H, J=7Hz), 1.50 to 1.70 (m, 3H), 1.75 to 2.17 (m, 3H), 2.17 to 2.53 (m, 3H), 3.38 to 3.72 m, 2H), 3.77 to 4.07 (m, 1H), 4.07 to 4.55 (m, 4H), 6.29 (s, 2H) and 7.12 to 7.40 (m, 5H).

Infrared absorption spectrum (KBr): 3220, 2977, 1745, 1725, 1640, 1570, 1450, 1380, 1238, 1190, 1000, 878 and 700 cm$^{-1}$ $[\alpha]_D^{25}$=-42.6 (c=1.0, MeOH).

What we claim is:

1. A process for preparing N-[1(S)-ethoxycarbonyl-3-phenylpropyl]-L-alanyl-L-proline, which comprises reacting an N-carboxyanhydride of N-[1(S)-ethoxycarbonyl-3-phenylpropyl]-L-alanine with L-proline in an amount of 1 to 1.5 moles of L-proline per mole of the N-carboxyanhydride in the presence of at least one base selected from the group consisting of an hydroxide of an alkali metal, a carbonate of alkali metal, an hydrogencarbonate of an alkali metal, a secondary amine, a tertiary amine and a quarternary ammonium hydroxide, in a mixture of water and an organic solvent, at a temperature of from −20° C. to room temperature and with pH of the reaction system maintained within an alkaline range.

2. The process of claim 1, wherein the organic solvent consists of at least one of acetone, dioxane, tetrahydrofuran and acetonitrile.

3. The process of claim 1, wherein the reaction is carried out while maintaining a pH of the reaction system within a range of from 9 to 10 in an aqueous medium.

4. The process of claim 1, wherein the reaction is carried out by adding N carboxyanhydride of N-[1(S)-ethoxycarbonyl-3-phenylpropyl]-L-alanine to a solution of a basic salt of L-proline.

5. The process of claim 1, wherein the organic solvent is ether.

6. The process of claim 1, wherein the organic solvent has a high compatibility with water.

* * * * *